(12) United States Patent
Green

(10) Patent No.: US 7,328,701 B2
(45) Date of Patent: Feb. 12, 2008

(54) VARIABLE SIZE ENDOTRACHEAL TUBE

(76) Inventor: Philip A. Green, 10545 Wilmer Ln SE., Olympia, WA (US) 98501

( * ) Notice: Subject to any disclaimer, the term of this patent is extended or adjusted under 35 U.S.C. 154(b) by 693 days.

(21) Appl. No.: 10/819,640

(22) Filed: Apr. 7, 2004

(65) Prior Publication Data

US 2005/0224079 A1 Oct. 13, 2005

(51) Int. Cl.
*A61M 11/00* (2006.01)
(52) U.S. Cl. .............................. 128/207.14; 128/207.17
(58) Field of Classification Search ..............................
128/207.14–207.17
See application file for complete search history.

(56) References Cited

U.S. PATENT DOCUMENTS

| | | | |
|---|---|---|---|
| 3,968,800 A | 7/1976 | Vilasi | |
| 4,586,505 A * | 5/1986 | Sisson et al. ............... | 606/192 |
| 4,827,925 A | 5/1989 | Vilasi | |
| 5,116,318 A * | 5/1992 | Hillstead ............... | 604/103.14 |
| 6,609,521 B1 | 8/2003 | Belani et al. | |
| 6,610,069 B2 | 8/2003 | Euteneuer et al. | |
| 6,616,690 B2 | 9/2003 | Rolando et al. | |
| 6,645,243 B2 | 11/2003 | Vallana et al. | |
| 6,655,377 B2 | 12/2003 | Pacey | |
| 6,668,832 B2 | 12/2003 | Hipolito et al. | |
| 6,676,691 B1 | 1/2004 | Hosny | |
| 6,679,911 B2 | 1/2004 | Burgermeister | |
| 6,685,721 B1 | 2/2004 | Kramer | |
| 7,144,408 B2 * | 12/2006 | Keegan et al. ............... | 606/200 |
| 2005/0183729 A1 * | 8/2005 | Fischer ................... | 128/207.29 |
| 2006/0157060 A1 * | 7/2006 | Nelson ................... | 128/207.14 |

* cited by examiner

*Primary Examiner*—Steven O. Douglas
(74) *Attorney, Agent, or Firm*—Darby & Darby PC; Jamie L. Wiegand

(57) ABSTRACT

A variable size endotracheal tube (VSET) is described for use in intubation of a body lumen. The VSET includes a flexible, tubular member with a distal end and a proximal end. The proximal end includes a tube adapter configured to be coupled to a gas source. In one embodiment, a stent-like infrastructure runs substantially longitudinally along the length of the tubular member. The stent-like infrastructure is configured to variably expand a cross-section of the inner surface of the tubular member along substantially the full length of the tubular member. Furthermore, the stent-like infrastructure is arranged to maintain the variable expansion of the cross-section to substantially prevent stenosis of the body lumen, while the body is intubated.

11 Claims, 8 Drawing Sheets

VARIABLE SIZE ENDOTRACHEAL TUBE

FIELD OF THE INVENTION

The present invention relates generally to endotracheal tubes, and more particularly, but not exclusively, to a variable size endotracheal tube for enabling rapid intubation.

BACKGROUND OF THE INVENTION

Endotracheal intubation includes the act of introducing a hollow tube, called an endotracheal tube, into a patient's trachea to provide airway control. Airway control is necessary for life in the unconscious patient or the patient who is unable to protect their own airway due to any variety of reasons. Endotracheal intubation allows ventilation of the unconscious patient, reduces aspiration risk, enables introduction of gases during surgery, presents an alternative drug route, and allows foreign body visualization and removal. In the emergency setting endotracheal intubation is time-critical, especially in instances where the patient is unable to breathe. Unfortunately, traditional approaches for endotracheal intubation are prone to at least two central problems, each of which frequently results in loss of life.

One such problem with traditional approaches of intubation is that a medical practitioner selects what they hope will be an appropriately sized endotracheal tube based upon the patient's body size. Should the patient's trachea be smaller than anticipated or become narrowed beyond where it can be visualized (as is often the case due to trauma, hemorrhage, allergic reaction, infection, anatomic disruption, vocal cord dysfunction, or the like) a standard sized tube may not pass without causing damage to the surrounding tissue or in worst case scenarios will not pass at all. Moreover, in cases where only a smaller tube may fit safely into the patient's trachea, the diameter of the endotracheal tube may be inadequate to provide the necessary pressure for ventilation and treatment. For example, the smaller tube size may make it harder for the patient to breathe, for the medical practitioner to administer sufficient medications, and the like, thereby further endangering the life of the patient.

Closely related to the issue of properly fitting the standard sized endotracheal tube into the patient's trachea is the lack of adequate visibility for proper intubation by the medical practitioner. During endotracheal intubation, the medical practitioner must have a certain level of visibility beyond the most distal end of the endotracheal tube in order to safely guide the tube past any obstructions and in between the vocal cords into the trachea. Unfortunately, visibility of the vocal cords and the entrance to the trachea is often obscured due to the relatively large size of the endotracheal tube itself as it is brought into position. At other times, visibility may be obscured due to any of a variety of reasons, including trauma, bleeding in the airway, tumor, infection, cord pathology, epiglottitis, and the like. Without sufficient visibility during intubation, the medical practitioner must often blindly guide the tube by approximating the entrance to the trachea, a process that is both dangerous and time-consuming. A blind intubation often results in placement of the endotracheal tube into the esophagus, which in turn results in the inability to ventilate the patient causing both morbidity and mortality. Current practices, that may involve such aids as mirrors, or the like, to enhance visibility, may unfortunately also require adding an extra width to the already cramped diameter of the tube, often further exacerbating the size problem.

Solutions to the problems of variable tube sizes and lack of adequate visibility during intubation are not currently within the scope of existing tools or methods, and therefore there is need in the industry for an improved tool and associated endotracheal intubation methods. Therefore, it is with respect to these considerations and others that the present invention has been made.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Invention, which is to be read in association with the accompanying drawings, wherein.

DETAILED DESCRIPTION OF THE PREFERRED EMBODIMENT

Figure 1:
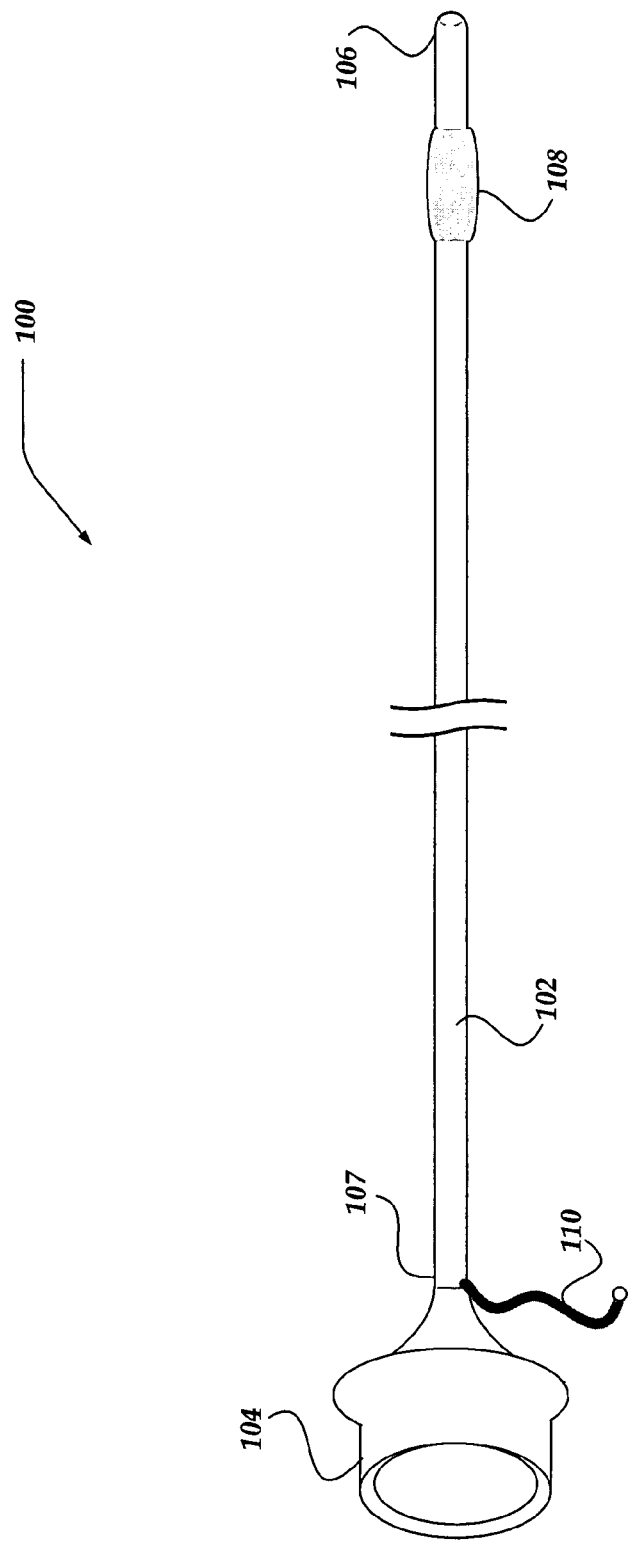
FIG. 1 illustrates an overall side view of one embodiment of an unexpanded Variable Size Endotracheal Tube (VSET)

The present invention now will be described more fully hereinafter with reference to the accompanying drawings, which form a part hereof, and which illustrate specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. The following detailed description is, therefore, not to be taken in a limiting sense.

The terms "tube," and "tubular," includes virtually any hollow member that may be of a substantially circular cross-sectional configuration or of any other cross-sectional configuration, including, but not limited to elliptical, oval, polygonal, and the like.

The phrase "in one embodiment," as used herein does not necessarily refer to the same embodiment, although it may. Moreover, the phrase "in another embodiment," as used herein does not necessarily refer to a different embodiment, although it may.

The term "based on" is not exclusive and provides for being based on additional factors not described, unless the context clearly dictates otherwise.

Briefly stated, the present invention is directed towards a variable size endotracheal tube for use in intubation of a body lumen, such as a patient's trachea, other body cavity, and the like. One embodiment of the variable size endotracheal tube includes a flexible, tubular member with a distal end and a proximal end. The proximal end includes a tube adapter configured to be coupled to a gas source. A stent-like infrastructure runs substantially longitudinally along the length of the tubular member. The stent-like infrastructure is configured to variably expand a cross-section of the inner surface of the tubular member along substantially its full length. Furthermore, the stent-like infrastructure is further configured to maintain the variable expansion of the cross-section to substantially prevent stenosis of the body lumen, while the body is intubated. The variable size endotracheal tube is configured for temporary intubation. The period of temporary use may vary, and the invention is not constrained to any particular period. However, a typical temporary use may be as short as a couple of minutes, or less, to as long as a couple of weeks.

Various delivery and expansion systems are presented that may be employed to assist in the insertion of the variable size endotracheal tube into the body lumen. The delivery and expansion systems are further employed to actuate the stent-like infrastructure causing it to expand radially outward, against the inner surface of the body lumen. The delivery and expansion systems may then be removed to enable a medial practitioner to provide a medical gas, air, and the like through the expanded variable size endotracheal tube.

By employing the present invention, a medical practitioner may quickly and safely intubate the body lumen, such as a trachea even in the presence of a partially narrowed airway. Because the present invention is configured to be variably expanded for various sized body lumens, the present invention may minimize the traditional problem of attempting to select an appropriately sized endotracheal tube for a given patient.

While the present invention is described in the form of an endotracheal tube, it is believed that those skilled in the art will readily recognize that as the description proceeds, such device may be utilized also for convenient insertion into, and removal from, any other body opening. Thus, the present invention is not limited to endotracheal tubes.

Illustrative Variable Size Endotracheal Tubes

FIG. 1 illustrates an overall side view of one embodiment of an unexpanded Variable Size Endotracheal Tube (VSET) 100. VSET 100 includes tubular member 102 with distal end 106 and proximal end 107. In one embodiment, distal end 106 is substantially beveled. VSET 100 further includes tube adapter 104, cuff conduit 110, and tracheal cuff 108. Tube adapter 104 is coupled to tubular member 102 at its proximal end 107.

Tracheal cuff 108 may comprise a thin walled, high volume, low-pressure chamber, vessel, bag-like structure, or the like, that is configured to be inflated and deflated.

Tracheal cuff 108 may be located in a position around an exterior circumference, of and near, distal end 106 of tubular member 102. Tracheal cuff 108 is typically arranged to engage an inner wall of a pharynx, larynx, trachea, or similar lumen, when inflated.

Cuff conduit 110 includes a small tube, channel, or the like, a distal end of which is attached to a proximal end of tracheal cuff 108. The proximal end of cuff conduit 110 is located near proximal end 107 of tubular member 102. A body length of cuff conduit 110 may run substantially seamlessly along the longitudinal length of tubular member 102. In one embodiment, cuff conduit 110 runs along the exterior surface of tubular member 102, however, the invention is not so limited. For example, cuff conduit 110 may also run along the inner surface of tubular member 102, without departing from the scope of the invention.

The proximal end of cuff conduit 110 may include an external inflation and deflation port which is adapted to receive a delivery mechanism, such as a syringe (not shown), or the like, which may be employed to inflate or deflate tracheal cuff 108. Cuff conduit 110 may be employed to inflate tracheal cuff 108 to cause a seal to be formed between the exterior surface of tubular member 102 and a patient's trachea to preclude a gas from escaping around tubular member 102 that may be forced into the patient's lungs, or other body lumen. Additionally, the seal formed by inflated tracheal cuff 108 within the patent's trachea, or other body lumen, may provide a barrier to a flow of blood, mucus, secretions, or the like, into the patient's lungs. Tracheal cuff 108, when inflated, may also be employed to stabilize VSET 100 within the trachea of the patient.

Although cuff conduit 110 and tracheal cuff 108 are illustrated, it is noted that neither are necessary components to the invention, and other components, configurations, and the like, may be employed to preclude inadvertent escaping of gas, stabilization of VSET 100, and the like. For example, tubular member 102 may be configured to expand sufficiently to provide substantially a similar function to cuff conduit 110.

Tube adapter 104 may be affixed to proximal end 107 of tubular member 102 employing virtually any manner that enables an airtight seal to be created at the point of attachment. Tube adapter 104 may be arranged to couple a gas supply tubing, gas source, or the like, to tubular member 102 to enable a desired medical gas, such as oxygen, an anesthetic gas, and the like, to be introduced to a patient, through tubular member 102 when tubular member 102 is expanded.

Tube adapter 104 may be composed of a single unitary flexible material, or of multiple materials, of which at least the end coupled to tubular member 102 comprises a substantially flexible material. Such substantially flexible material may be arranged to expand or contract in response to a variation in size of a cross-section of proximal end 107. Tube adapter 104 may change shape to ensure that it remains coupled to tubular member 102, forming a substantially airtight seal. As illustrated in FIG. 1, tube adapter 104 is in a contracted state.

Tubular member 102 may be virtually any tube-like elongated device having an essentially hollow interior that may be utilized as a substitute for a glottic airway when inserted into a patient's trachea and selectively expanded to approximately an inner diameter of the body lumen, such as the trachea, or the like.

Tubular member 102 may comprise virtually any biocompatible elastomeric material. For example, tubular member 102 may include a flexible, elastic medical grade material, including, but not limited to, rubber, soft plastic, elastic polyvinyl chloride, silicone elastomer, elastic polyurethane, latex, and the like, that enables expansion of a cross-section of tubular member 102 along substantially its full length in response to selective operation as described further below.

Tubular member 102 may further be coated with a lubricant, or similar material that aids in the insertion of VSET 100 into the patient's body lumen, with minimal abrasion, or other damage.

Tubular member 102 is configured to include a stent-like infrastructure (not shown) that extends along substantially its full length. The detail of one embodiment of this stent-like infrastructure is described below in conjunction with FIG. 2. Briefly, however, the stent-like infrastructure is arranged to expand a cross-section of an inner surface of tubular member 102 from a substantially collapsed state to a selectively expanded state. As illustrated in FIG. 1, tubular member 102 is in a substantially collapsed state having a minimum outer diameter.

In its collapsed state, tubular member 102 is configured to retain a lumen that extends its entire length. The lumen is adapted to receive a flexible delivery and expansion system through the entire length of tubular member 102. Various embodiments of flexible delivery and expansion systems are described in more detail below in conjunction with FIGS. 3-6.

Tubular member 102 may be expanded along the cross-section of its inner surface to a variety of dimensions to make its outer diameter closely proximate the size of a patient's glottis, or opening between the vocal cords, and the like. As such, in one embodiment tubular member 102 may be variably expanded to an internal diameter of about 3.5 mm to about seven mm to accommodate a child, from about seven mm to about 11 mm to accommodate an adult, and the like. However, the inner dimensions are not constrained to these inner diameters, and tubular member 102 may be configured to expand to other inner diameters, without departing from the present invention.

Tubular member 102 may include virtually any length that is sufficient for insertion into a patient's trachea reaching sufficiently near a trachea caring, and extending from a patient's mouth with a sufficient length for manipulation. In one embodiment, tubular member 102 ranges between about three to five inches for a child, and about eight to 11 inches for an adult.

Figure 2:
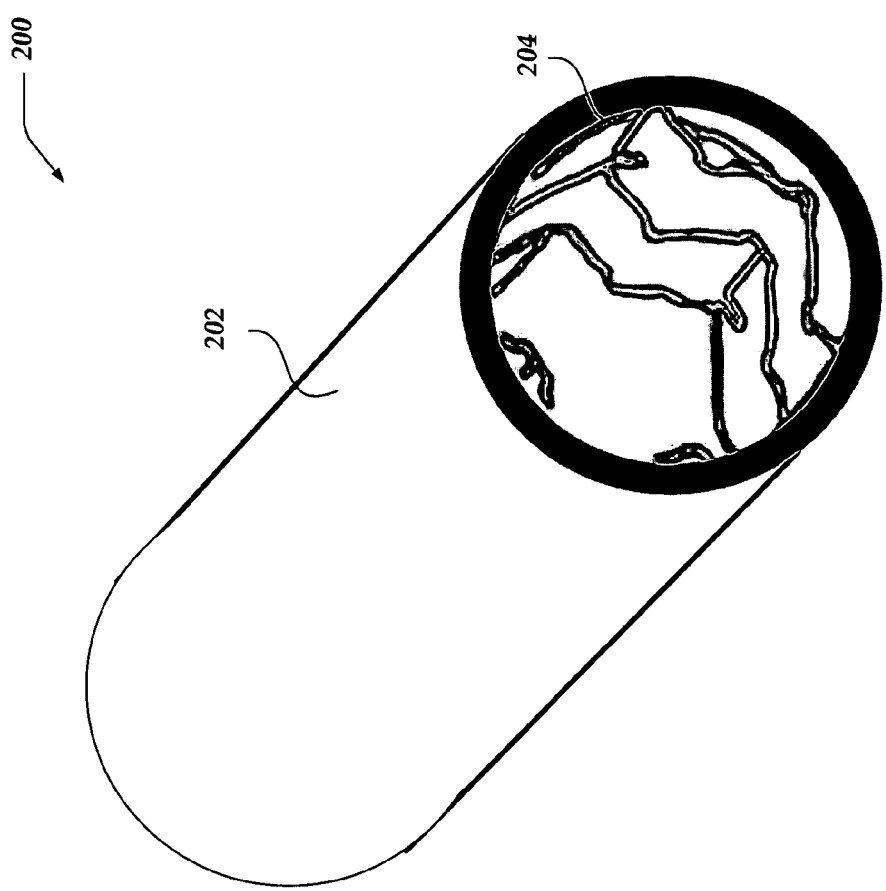
FIG. 2 illustrates a cross-sectional view of one embodiment of a tubular member of the VSET employing a stent-like infrastructure.

FIG. 2 illustrates a cross-sectional view of one embodiment of a tubular member of the VSET employing a stent-like infrastructure. As shown in FIG. 2, tubular member 200 includes outer membrane 202 and stent-like infrastructure 204.

Outer membrane 202 may comprise a substantially uninterrupted relatively smooth outer surface configured to vary radially outward in size along substantially its full length.

Stent-like infrastructure 204 comprises a generally tubular framework with a wall having a substantially looped or mesh-like apertured structure. Stent-like structure 204 is configured to extend substantially along the length of tubular member 200. In one embodiment, stent-like infrastructure 204 is substantially similar to an angioplasty stent with the ability to expand to an approximate size of an inner dimension of a patient's trachea, or similar body lumen.

Stent-like infrastructure 204 is capable of being dilated in use from a radially contracted state of about one to about two millimeters, to a radially expanded state of about 3.5 millimeters to about 11 millimeters. The invention is not limited to any specific dimensions, however, and other dimensions may be selected, such that the outer diameter of tubular member 200 may be radially contracted to allow VSET 100 of FIG. 1 to be introduced into the trachea in a manner that enables quick and ready viewing of the epiglottal region, and the expanded diameter corresponds in general to the diameter to be established and maintained in the body lumen.

Moreover, stent-like infrastructure 204 is further configured to maintain its radially expanded state, substantially preventing stenosis of a body lumen, such as a patient's trachea.

Stent-like infrastructure 204 may include virtually any material capable of withstanding compression and dilation without losing its structural integrity. For example, stent-like infrastructure 204 may include a variety of metals, such as steel, American Iron and Steel Institute's AISI 316 steel, AISI 316 L, and the like, a shape memory material, such as that known by its trade name of "Nitinol," similar superelastic material, and the like.

Although outer membrane 202 and stent-like infrastructure 204 are illustrated in FIG. 2 as two distinct components, the present invention is not so limited. For example, in one embodiment, stent-like infrastructure 204 is integrated within outer membrane 202 to appear as a single component.

Figure 3:
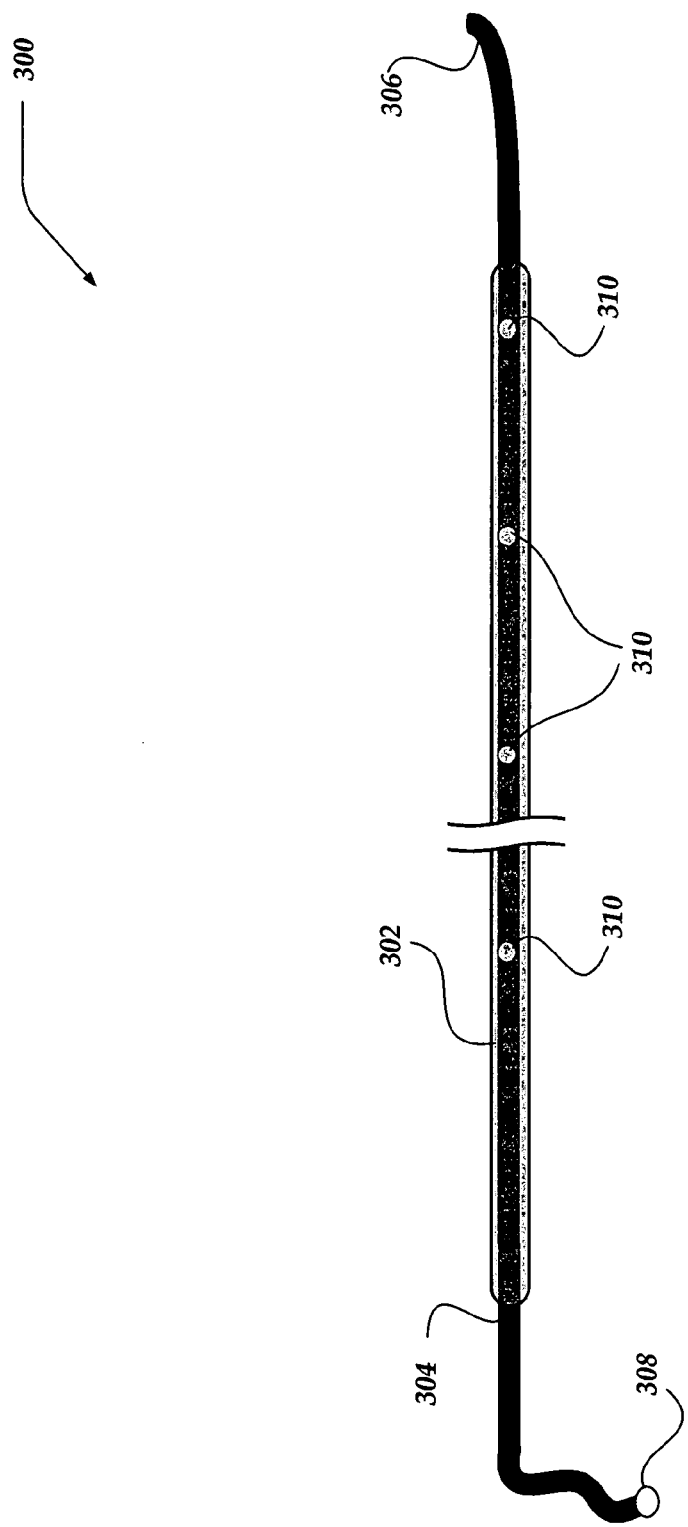
FIG. 3 illustrates one embodiment of an delivery and expansion system in an unexpanded state for use in expanding the VSET of FIG. 1.

FIG. 3 illustrates one embodiment of a delivery and expansion system for use in expansion of VSET 100 of FIG. 1. Not all of the components may be required to practice the invention, and variations in the arrangement and type of the components may be made without departing from the spirit or scope of the invention.

As shown in FIG. 3, Delivery and Expansion System (DES) 300 includes balloon 302 in a collapsed state, hollow guidewire 304, semi-flexible tip 306, and inflation tube 308, and perforations 310.

Semi-flexible tip 306 is affixed to a distal end of hollow guidewire 304 employing virtually any manner that enables an airtight seal to be created at the point of attachment. Semi-flexible tip 306 is configured to be sufficiently firm to assist the medical practitioner in guiding hollow guidewire 304 and VSET 100 of FIG. 1 into a proper location of the patient's trachea, yet sufficiently soft to flex and bend upon itself to minimize damage to the patient. Semi-flexible tip 306 may comprise virtually any semi-flexible material, including, but not limited to, rubber, rubber coated metal, and the like. A length of semi-flexible tip 306 is typically about one to about three inches, although semi-flexible tip 306 may be of virtually any length without departing from the scope of the invention.

Balloon 302 may be affixed substantially around the outer circumference of hollow guidewire 304. Balloon 302 may be configured to run substantially longitudinally along the length of hollow guidewire 304 for a length approximately that of VSET 100 of FIG. 1. Balloon 302 may comprise virtually any elastic material, including rubber, latex, polyethylene, and the like.

Balloon 302 may be affixed to hollow guidewire 304 employing virtually any means known in the industry, including, but not limited to adhesives, pinning, stabling, heat fusion, and the like. For example, in one embodiment, balloon 302 and hollow guidewire 304 are constructed as a single component.

In one embodiment, balloon 302 is substantially similar to a balloon that may be employed for angioplasty stent expansion, but sufficiently sized to variably expand VSET 100 of FIG. 1 for a patient's trachea, or similar body lumen.

Hollow guidewire 304 may comprise any semi-flexible material suitable for guiding VSET 100 of FIG. 1 into a patient's trachea without inflicting damage to the patient or VSET 100. Hollow guidewire 304 may comprise, for example, a hollow tubing of wire such as copper, semi-flexible plastic, rubber, and the like.

It is desirable that the outer diameter of hollow guidewire 304 be made as small as possible, to enable VSET 100 to be as thin as possible. In one embodiment, hollow guidewire 304 is about the outer circumference of a traditional wire coat hanger, or approximately two mm to about five mm, or similar approximations. Moreover, it is desirable to make the lumen traversing the length of hollow guidewire 304 to be as large in inner circumference as is reasonable, to ensure as rapid an expansion of balloon 302 as possible without damage.

Hollow guidewire 304 may be of a length sufficient to extend beyond both the distal and proximal ends of VSET 100. As such, hollow guidewire 304 may be similarly sized to accommodate the patient. For example, in one embodiment, hollow guidewire 304 may be between about four inches to about six inches for a child, and about nine to about 12 inches for an adult, with an additional length sufficient to enable the medical practitioner to negotiate VSET 100 into a proper location of the patient's trachea.

Figure 4:
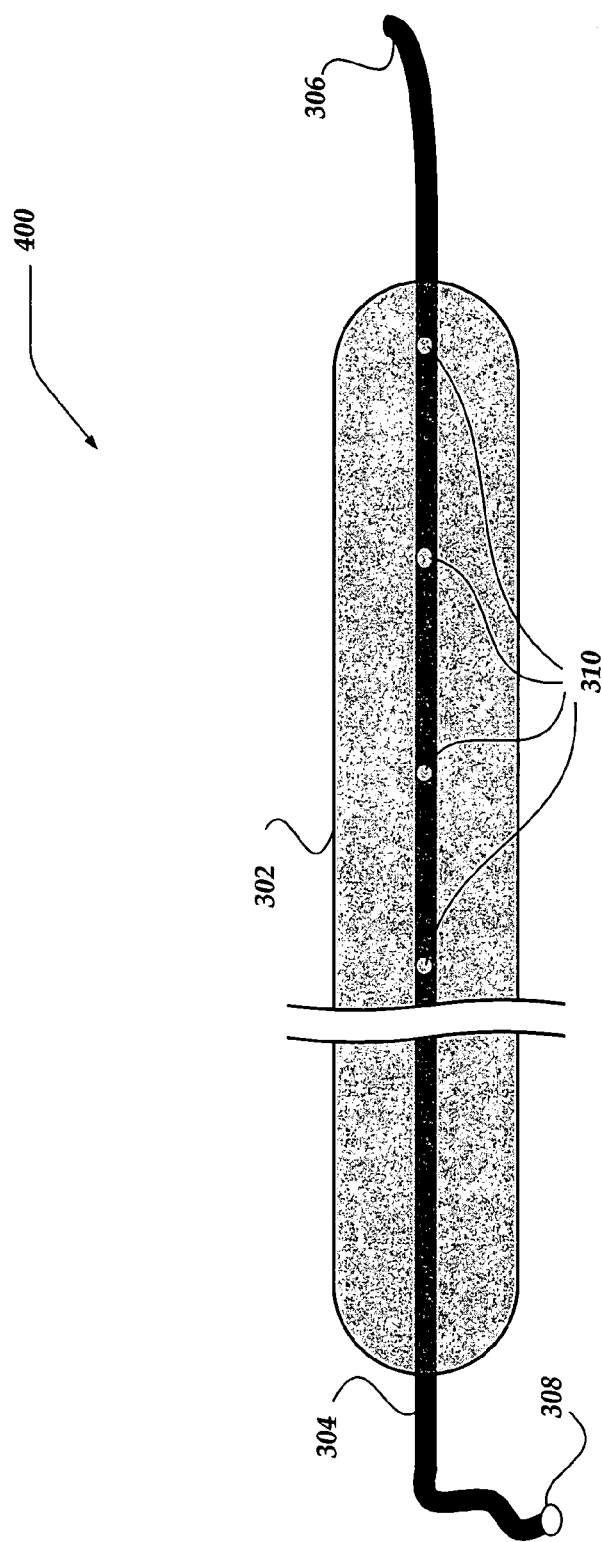
FIG. 4 illustrates one embodiment of the delivery and expansion system of FIG. 3 in an expanded state.

Hollow guidewire 304 includes at least one perforation 310 along its length and under balloon 302. Perforations 310 are adapted to enable a fluid, such as a gas, liquid, or the like, to flow from the lumen of hollow guidewire 304 into balloon 310 to enable balloon 310 to expand as illustrated in FIG. 4.

Inflation tube 308 is affixed to the proximal end of hollow guidewire 304 employing virtually any manner that enables an airtight seal to be created at the point of attachment. Inflation tube 308 is adapted to enable a syringe or other delivery mechanism to be attached. When the delivery mechanism is attached to one end of inflation tube 308, the fluid may be injected through inflation tube 308 and into the lumen of hollow guidewire 304. Perforations 310 then allow the fluid to enter and expand balloon 302. In its expanded state, balloon 302 is configured to apply a sufficient force against the inner luminal surface of tubular member 102 of FIG. 1, actuating its stent-like infrastructure to quickly, but safely expand the cross-section of the inner surface of tubular member 102. By adjusting the flow and quantity of fluid into balloon 302, the medical practitioner may vary the expansion diameter of tubular member 102.

The present invention is not constrained to the details and mechanics as described above in conjunction with FIGS. 2-3, and the overall construction may vary without departing from the scope or spirit of the invention. For example, illustrated in FIG. 5 is one embodiment of another expansion mechanism for use in expanding the VSET 100 of FIG. 1.

Figure 5:
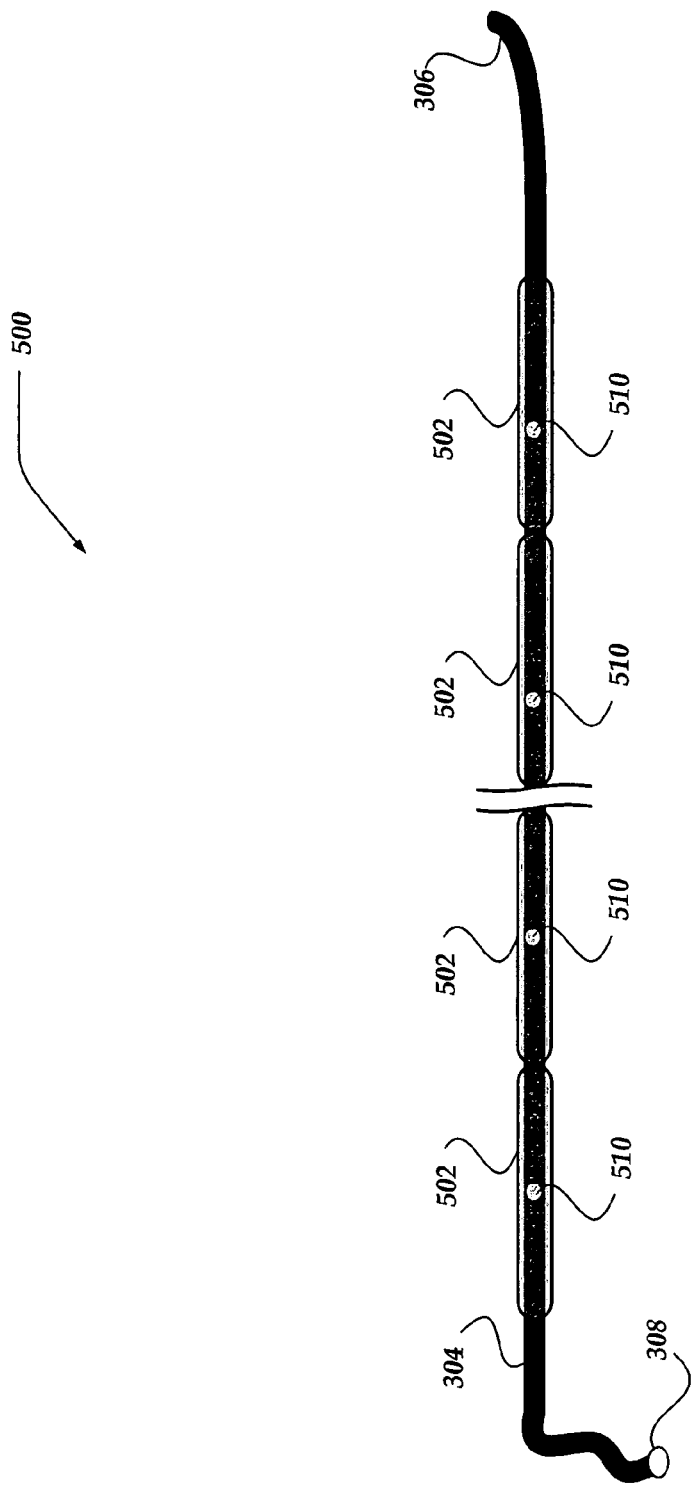
FIG. 5 illustrates one embodiment of another delivery and expansion system for use in expanding the VSET of FIG. 1.

As shown in FIG. 5, Delivery and Expansion System (DES) 500 includes a plurality of balloons 502 in collapsed states, hollow guidewire 304, semi-flexible tip 306, and inflation tube 308, and perforations 510. Hollow guidewire 304, semi-flexible tip 306, and inflation tube 308 may be substantially similar to those described above in conjunction with FIG. 3. Moreover, DES 500 may operate substantially similar to DES 300, except that DES 500 employs a plurality of balloons to actuate the expansion of VSET's stent-like infrastructure and DES 300 employs a single balloon.

Figure 6:
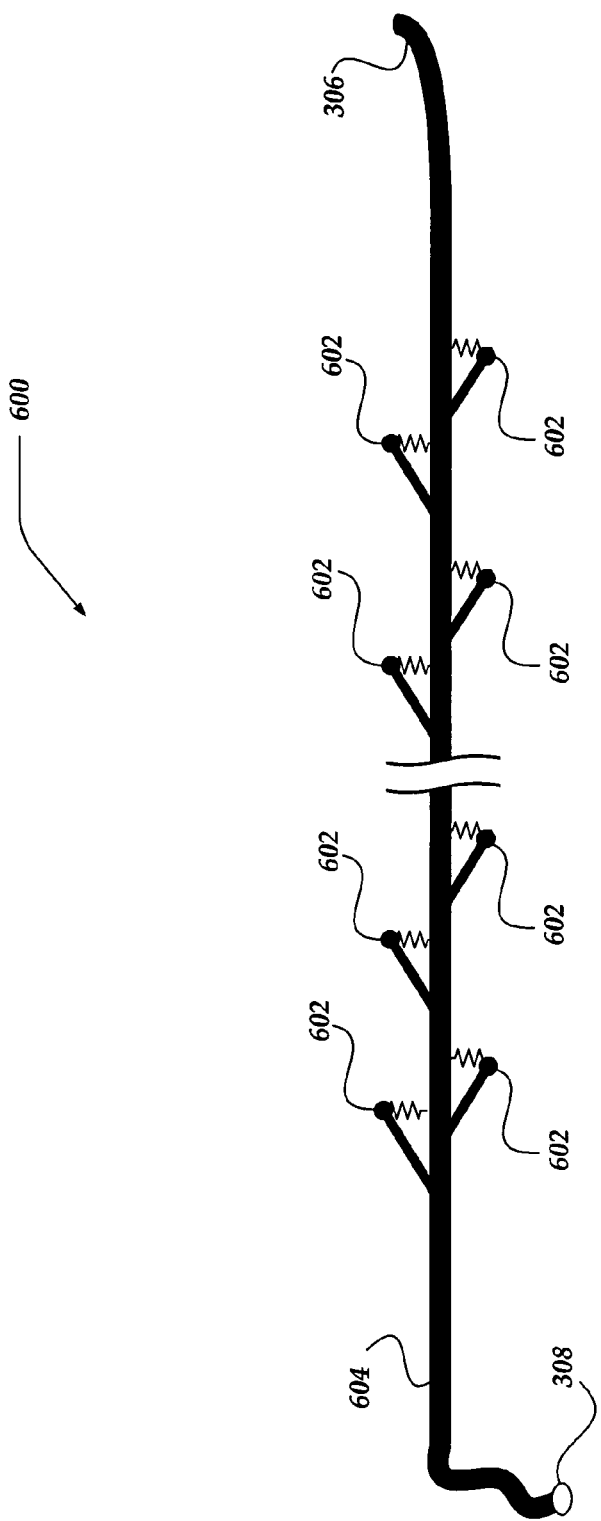
FIG. 6 illustrates one embodiment of yet another delivery and expansion system for use in expanding the VSET of FIG. 1.

FIG. 6 illustrates one embodiment of yet another delivery and expansion for use in expanding VSET 100 of FIG. 1. As shown in FIG. 6, Delivery and Expansion System (DES) 600 includes inflation tube 308, hollow guidewire 604, spring-loaded levers 602, and semi-flexible tip 306.

Semi-flexible tip 306 is affixed to a distal end of hollow guidewire 604 employing virtually any manner that enables an airtight seal to be created at the point of attachment. Semi-flexible tip 306 is configured to be sufficiently firm to assist the medical practitioner in guiding hollow guidewire 604 and VSET 100 of FIG. 1 into a proper location of the patient's trachea, yet sufficiently soft to flex and bend upon itself to minimize damage to the patient. Semi-flexible tip 306 may be substantially similar to semi-flexible tip 306 of FIG. 3.

Spring-loaded levers 602, shown in FIG. 6 in their expanded states, may be affixed substantially around an outer radial circumference of hollow guidewire 604. Spring-loaded levers 602 may be spaced appropriately apart from each other in such a way as to allow a substantially even expansion of VSET 100 in FIG. 1. Spring-loaded levers 602 may comprise virtually any medically safe, semi-rigid material, including rubber, plastic, plastic coated metal, and the like.

Although the term "spring-loaded" is used here to describe "spring-loaded" levers 602, it is understood that spring-loaded levers 602 may be brought from unexpanded states, in which they lie relatively flush with the outer surface of hollow guidewire 604, to expanded states, in which they expand VSET 100 in FIG. 1, by way of virtually any mechanism without departing from the scope of the invention. For example, spring-loaded levers 602 may be expanded through the use of springs, pumps, hydraulics, gears, electrical circuitry, and the like. In addition, spring-loaded levers 602 may be affixed to hollow guidewire 604 employing virtually any means known in the industry, including, but not limited to, adhesives, pinning, stabling, heat fusion, and the like. For example, in one embodiment, spring-loaded levers 602 and hollow guidewire 604 are constructed as a single component.

Hollow guidewire 604 may comprise any semi-flexible material suitable for guiding VSET 100 of FIG. 1 into a patient's trachea without inflicting damage to the patient or VSET 100 of FIG. 1. Hollow guidewire 604 may be substantially similar to hollow guidewire 304 of FIG. 3.

In one embodiment, inflation tube 308 is affixed to the proximal end of hollow guidewire 604 employing virtually any manner that enables an airtight seal to be created at the point of attachment. Inflation tube 308 may be adapted to enable a syringe or other delivery mechanism to be attached. When the delivery mechanism is attached to one end of inflation tube 308, the fluid may be injected through inflation tube 308 and into the lumen of hollow guidewire 604. Mechanisms within hollow guidewire 604 then expand spring-loaded levers 602. In their expanded states, spring-loaded levers 602 force against the inner luminal surface of tubular member 102 of FIG. 1, actuating its stent-like infrastructure to quickly, but safely expand the cross-section of the inner surface of tubular member 102.

In another embodiment, inflation tube 308 may include an electrical/mechanical mechanism that may be employed to activate spring-loaded levers 602. In this embodiment, hollow guidewire 604 may include an electrical, mechanical, or a combination of electrical/mechanical mechanisms, wires, and the like, running substantially its inner length.

It should be noted that the present invention does not limit the methods of expanding spring-loaded levers 602 to the injection of a fluid, such as a gas, and the like, but also allows for electrical impulses, heat, and like to trigger internal mechanisms to automatically expand spring-loaded levers 602. For example, in one embodiment, spring-loaded levers 602 may be held in their unexpanded states by internal restraints that, when exposed to an electrical current, melt or otherwise cease to further restrain spring-loaded levers 602, causing spring-loaded levers 602 to expand against the cross-section of the inner surface of tubular member 102 in FIG. 1.

Illustrative Method for Use of the Variable Size Endotracheal Tube

One embodiment of a general method for use of the present invention is next described by reference to FIGS. 7-8.

Figure 7:
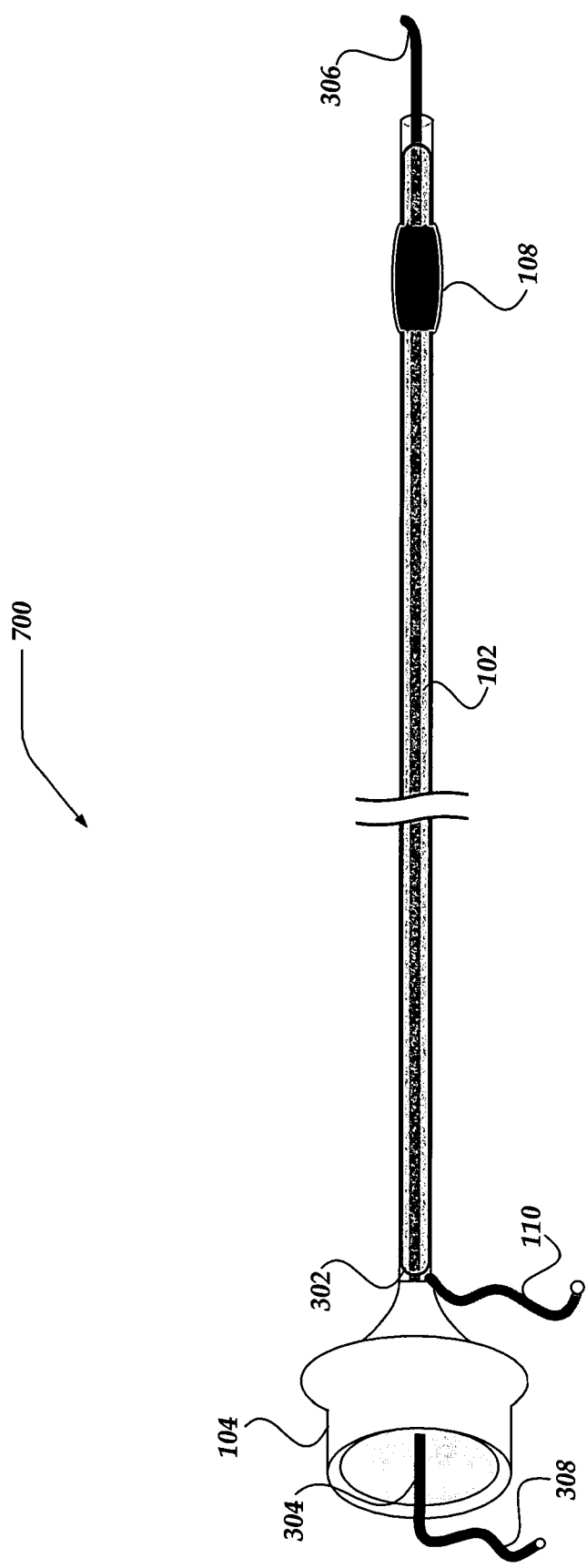
FIG. 7 illustrates one embodiment for integrating a delivery and expansion system into the VSET of FIG. 1 in their unexpanded states.
Figure 8:
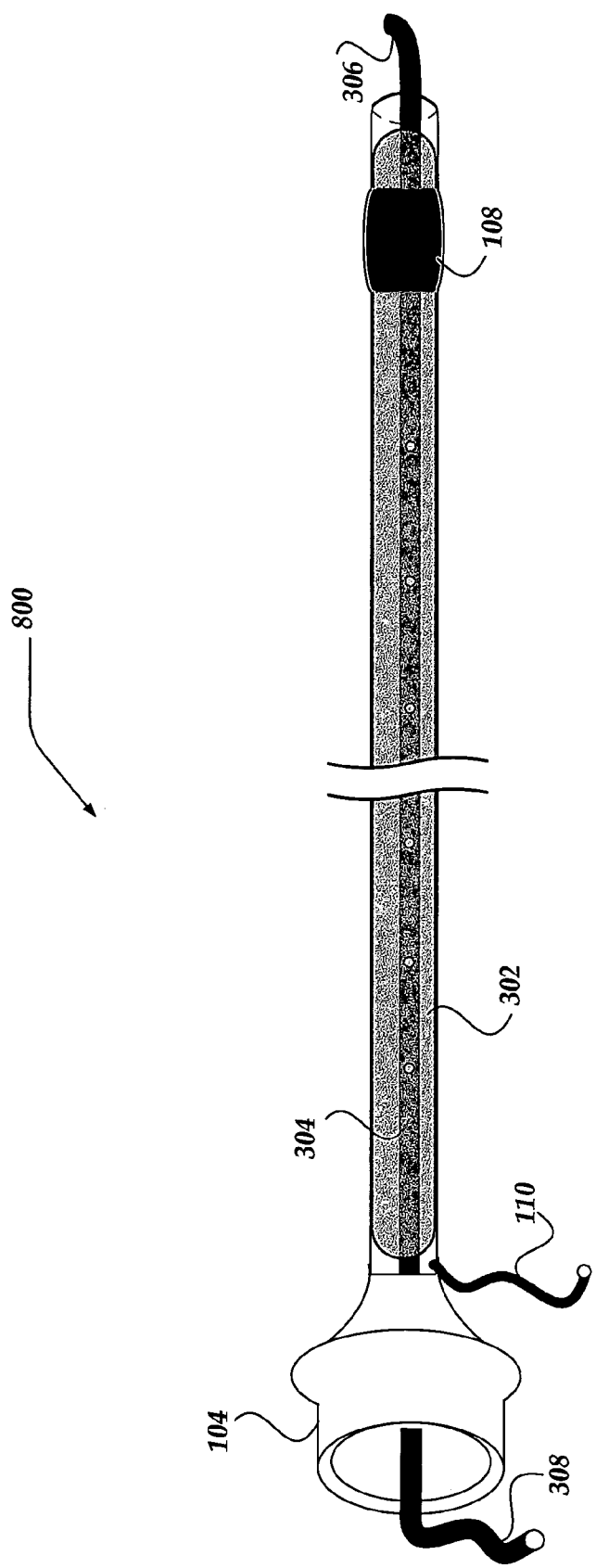
FIG. 8 generally illustrates one embodiment of the delivery and expansion system and VSET of FIG. 7 in their expanded states, in accordance with the present invention.

FIG. 7 illustrates one embodiment for integrating a delivery and expansion system into VSET 100 of FIG. 1 in their unexpanded states. As shown in the figure, use is made of DES 300 of FIG. 3. However, the invention is not so limited and other delivery and expansion systems may be employed, without departing from the scope or spirit of the invention.

As shown in FIG. 7, integrated assembly 700 includes a hollow guidewire 304 that s positioned inside the lumen of tubular member 102 of the VSET, such that semi-flexible tip 306 extends beyond the distal end of the VSET and inflation tube 308 extends beyond the proximal end of the VSET. VSET may be gently crimped, or otherwise temporarily secured, onto hollow guidewire 304 and over balloon 302 either by hand or with a tool such as a pliers, or the like to be mounted for deliver such as shown in FIG. 7. The physician may perform the crimping prior to intubation, during manufacturing, or virtually any time prior to use.

The distal end of integrated assembly 700 may be inserted into, for example, the nose, or mouth of the patient. When integrated assembly 700 is inserted into the mouth, various assists may be employed to hold open the mouth. Additionally, semi-flexible tip 306 may be employed to gently and safely guide integrated assembly 700 into the patient's trachea towards the caring, or other anatomical structure. As integrated assembly 700 is in a highly contracted state, viewing of the patient's airway is greatly improved over the use of traditional endotracheal tubes.

After alignment of integrated assembly 700, inflation tube 308 may be attached to a syringe or other delivery mechanism. A fluid may be injected through inflation tube 308 into the lumen of hollow guidewire 304. The fluid may then flow through the perforations of hollow guidewire 304 and into balloon 302, actuating the stent-like infrastructure of tubular member 102. The actuation of the stent-like infrastructure in turns causes tubular member 102 to quickly, but safely to expand radially outward as illustrated in FIG. 8. By proper adjustment of the injected fluid, the outer diameter of tubular member 102 may be varied to accommodate differing sizes of tracheas.

After tubular member 102 is sufficiently inflated, the delivery and expansion system may be withdrawn. The stent-like infrastructure retains the selective expansion of tubular member 102 to substantially prevent stenosis of the patient's trachea. Additionally, trachea cuff 108 may be inflated to assist in maintaining the positioning of the VSET.

The above specification, examples, and data provide a complete description of the manufacture and use of the composition of the invention. Since many embodiments of the invention can be made without departing from the spirit and scope of the invention, the invention resides in the claims hereinafter appended.

I claim:

1. A medical device adapted for insertion into a trachea, comprising:
   a temporary use, flexible, longitudinally extending tubular member having a stent-like infrastructure extending substantially the length of the tubular member; and
   an actuator for selectively expanding radially outwards the stent-like infrastructure such that a cross-section of an inner surface of the tubular member is expanded and the stent-like infrastructure maintains the selective expansion, and wherein the actuator further comprises:
   a semi-flexible guidewire having a lumen and at least one perforation extending from the lumen through the outer surface of the guidewire; and
   a balloon affixed substantially around the outer circumference of the guidewire, and configured to inflate radially outwards to a selective diameter in response to a flow of fluid from the at least one perforation.

2. The medical device of claim 1, wherein the actuator further comprises at least one balloon.

3. The medical device of claim 1, wherein the stent-like infrastructure further comprises a substantially tubular framework having a substantially mesh-like apertured structure.

4. The medical device of claim 1, wherein the stent-like infrastructure further comprises a stent.

5. The medical device of claim 1, wherein the stent-like infrastructure further comprises at least one of steel, a shape-memory material, and a super-elastic material.

6. The medical device of claim 1, wherein the tubular member further comprises a substantially uninterrupted relatively smooth outer surface configured to vary in cross-section along substantially its full length.

7. The medical device of claim 1, wherein the tubular member further comprises a medical grade material, comprising, in part, at least one of rubber, plastic, elastic polyvinyl chloride, silicone elastomer, elastic polyurethane, and latex.

8. The medical device of claim 1, wherein the tubular member is coated with a lubricant.

9. An endotracheal tube, comprising:
   a flexible, longitudinally extending tubular member including an infrastructure configured to vary a cross-section of an inner surface from a substantially collapsed state to a substantially permanent, selectively expanded state;
   a semi-flexible guidewire having a lumen and at least one perforation extending from the lumen through the outer surface of the guidewire; and
   at least one balloon affixed substantially around the outer circumference of the guidewire, and configured to inflate radially outwards to a selective diameter in response to a flow of fluid from the at least one perforation.

10. The endotracheal tube of claim 9, wherein the infrastructure further comprises a substantially tubular framework having a substantially mesh-like apertured structure.

11. A method of intubating a body lumen, comprising:
    obtaining a variable size endotracheal tube comprising a flexible, longitudinally extending tubular member having a stent-like infrastructure extending substantially the length of the tubular member;
    inserting into the tubular member an actuator for selectively expanding the stent-like infrastructure;
    inserting a distal end of the variable size endotracheal tube into the body lumen;
    employing an expansion system to selectively expand the stent-like infrastructure of the variable size endotracheal tube to accommodate an inner wall of the body lumen; and
    withdrawing the expansion system, to enable the stent-like infrastructure to substantially maintain the selective expansion of a cross-section of an inner surface of the tubular member.

* * * * *